(12) United States Patent
Feldkamp

(10) Patent No.: US 9,207,197 B2
(45) Date of Patent: Dec. 8, 2015

(54) COIL FOR MAGNETIC INDUCTION TO TOMOGRAPHY IMAGING

(71) Applicant: Kimberly-Clark Worldwide, Inc., Neenah, WI (US)

(72) Inventor: Joseph R. Feldkamp, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 149 days.

(21) Appl. No.: 14/191,941

(22) Filed: Feb. 27, 2014

(65) Prior Publication Data
US 2015/0241373 A1    Aug. 27, 2015

(51) Int. Cl.
*G01N 27/02*    (2006.01)
*H01F 27/30*    (2006.01)
*H01F 27/28*    (2006.01)

(52) U.S. Cl.
CPC .......... *G01N 27/023* (2013.01); *H01F 27/2823* (2013.01); *H01F 27/303* (2013.01)

(58) Field of Classification Search
CPC .................................................. A61B 5/0522
USPC .................... 324/228, 243, 240; 333/131, 124
See application file for complete search history.

(56) References Cited

U.S. PATENT DOCUMENTS

| | | | |
|---|---|---|---|
| 5,144,236 A | 9/1992 | Strenk | |
| 5,818,232 A | 10/1998 | Mehr et al. | |
| 6,865,494 B2 | 3/2005 | Duensing et al. | |
| 7,839,147 B2 | 11/2010 | Katscher et al. | |
| 7,923,995 B2 | 4/2011 | Schulz | |
| 8,115,488 B2 | 2/2012 | McDowell | |
| 8,125,220 B2 * | 2/2012 | Igney et al. | ............ 324/240 |
| 8,384,378 B2 | 2/2013 | Feldkamp et al. | |
| 8,423,129 B2 | 4/2013 | Waffenschmidt et al. | |
| 8,452,388 B2 | 5/2013 | Feldkamp et al. | |

(Continued)

FOREIGN PATENT DOCUMENTS

CN    102499681    6/2012
CN    102499682    6/2012

(Continued)

OTHER PUBLICATIONS

PCT International Search Report for corresponding PCT Application No. PCT/IB2014/063152, mailed on Dec. 8, 2014, 3 pages.

(Continued)

*Primary Examiner* — Louis Arana
(74) *Attorney, Agent, or Firm* — Dority & Manning, P.A.

(57) ABSTRACT

A coil for facilitating magnetic induction tomography imaging of a specimen, such as a human tissue specimen, using a single coil is provided. The coil can include a plurality of concentric conductive circular loops. The concentric conductive loops can be connected in series with connection traces without allowing the connection traces to distort the fields produced by the plurality of concentric conductive circular loops. The plurality of concentric conductive loops can be arranged in multiple planes (e.g. on a multilayer printed circuit board) as a two layer stack. The spacing between the planes or the plane separation distance can be selected such that mathematically the plurality of conductive loops can be treated as being located in a common plane for purposes of a quantitative analytical model used for magnetic induction tomography imaging.

22 Claims, 8 Drawing Sheets

(56) References Cited

U.S. PATENT DOCUMENTS

| | | |
|---|---|---|
| 2004/0079485 A1 | 4/2004 | Lee et al. |
| 2004/0124779 A1 | 7/2004 | Howald et al. |
| 2006/0125475 A1 | 6/2006 | Sodickson et al. |
| 2008/0258717 A1 | 10/2008 | Igney et al. |
| 2009/0102480 A1 | 4/2009 | Katscher et al. |
| 2009/0219289 A1 | 9/2009 | Kalvin |
| 2010/0127705 A1* | 5/2010 | Scharfetter ............... 324/310 |
| 2011/0004432 A1 | 1/2011 | Chen et al. |
| 2011/0007937 A1 | 1/2011 | Yan et al. |
| 2011/0133729 A1 | 6/2011 | Vernickel et al. |
| 2011/0133731 A1 | 6/2011 | Vauhkonen et al. |
| 2011/0172512 A1 | 7/2011 | Yan et al. |
| 2011/0282609 A1 | 11/2011 | Liu et al. |
| 2011/0313277 A1 | 12/2011 | Igney et al. |
| 2012/0019238 A1 | 1/2012 | Eichardt et al. |
| 2012/0101773 A1 | 4/2012 | Mcewan et al. |
| 2012/0150458 A1 | 6/2012 | Sodickson et al. |
| 2012/0153943 A1 | 6/2012 | Jin et al. |
| 2012/0161782 A1 | 6/2012 | Ross |
| 2012/0169333 A1 | 7/2012 | Katscher et al. |
| 2015/0238114 A1* | 8/2015 | Feldkamp et al. ... A61B 5/0522 |
| 2015/0241372 A1* | 8/2015 | Feldkamp et al. ... A61B 5/0522 |

FOREIGN PATENT DOCUMENTS

| | | |
|---|---|---|
| CN | 103033847 | 4/2013 |
| EP | 2332463 | 6/2011 |
| EP | 2333587 | 6/2011 |
| JP | 2005-124692 | 5/2005 |
| RU | 2129406 | 4/1999 |
| WO | WO 2004-026136 A1 | 4/2004 |
| WO | WO 2005057467 | 6/2005 |
| WO | WO 2009138934 | 11/2009 |
| WO | WO 2009144461 | 12/2009 |
| WO | WO 2010003162 | 1/2010 |
| WO | WO 2010023586 | 3/2010 |
| WO | WO 2010052609 | 5/2010 |
| WO | WO 2010097726 | 9/2010 |
| WO | WO 2011161571 | 12/2011 |
| WO | WO 2012104799 | 8/2012 |

OTHER PUBLICATIONS

Feldkamp et al., "Effects of Extermity Elevation and Health Factors on Soft Tissue Electrical Conductivity", Measurement Science Review, vol. 9, No. 6, Jan. 2009, pp. 169-178.

Gabriel et al., "The Dielectric Properties of Biological Tissues: I. Literature Survey", Physics in Medicine and Biology, vol. 41, No. 11, Nov. 1996, pp. 2231-2249.

Gonzalez et al., "Volumetric Electromagnetic Phase-Shift Spectroscopy of Brain Edema and Hematoma", PloS ONE, vol. 8, Issue 5, May 14, 2013, 10 pages.

Guardo et al., "Contactless Measurement of Thoracic Conductivity Changes by Magnetic Induction", Proceedings of the19th International Conference IEEE/EMBS. vol. 6, Oct. 30-Nov. 2, 1997, Chicago, Illinois, pp. 2450-2453.

Haemmerich et al., "In Vivo Electrical Conductivity of Hepatic Tumours", Physiological Measurements, vol. 24, No. 2, May 2003, pp. 251-260.

Harpen et al., "Influence of Skin Depth on NMR Coil Impedance, Part II", Physics in Medicine and Biology, vol. 33, No. 5, May 1988, pp. 597-605.

Lionheart et al., Sensitivity Analysis of 3D Magnetic Induction Tomography (MIT), $3^{rd}$ World Congress on Industrial Process Tomography, Sep. 2-5, 2003, Banff, Alberta, Canada, pp. 239-244.

Luis et al., "Magnetic Inductance Tomography Imaging Using Tikhonov Regularization", Workshop on Inverse Obstacle Problems, Nov. 4-6, 2002, Lisbon, Portugal, 4 pages.

Netz et al., "Contactless Impedance Measurement by Magnetic Induction—A Possible Method for Investigation of Brain Impedance", Physiological Measurement, vol. 14, No. 4, Nov. 1993, pp. 463-471.

Puwal et al., "Fourier-Based Magnetic Induction Tomography for Mapping Resistivity", Journal of Applied Physics, vol. 109, No. 1, Jan. 1, 2011, pp. 014701-1-014701-5.

Soleimani et al., "Forward Problem in 3D Magnetic Induction Tomography (MIT)", $3^{rd}$ World Congress on Industrial Process Tomography, Sep. 2-5, 2003, Banff, Alberta, Canada, pp. 275-280.

Wei et al., "Electromagnectic Tomography for Medical and Industrial Applications: Challenges and Opportunities," Proceedings of the IEEE, vol. 101, No. 3, Mar. 2013, pp. 559-565.

Wei et al., "Three-Dimensional Magnetic Induction Tomography Imaging Using a Matrix Free Krylov Subspace Inversion Algorithm", Progress in Electromagnetics Research, vol. 122, Jan. 2012, pp. 29-45.

Zaman et al., "The Impedance of a Single-Turn Coil Near a Conducting Half Space", Journal of Nondestructive Evaluation, vol. 1, No. 3, Aug. 1980, pp. 183-189.

* cited by examiner

COIL FOR MAGNETIC INDUCTION TO TOMOGRAPHY IMAGING

FIELD OF THE INVENTION

The present disclosure relates generally to the field of magnetic induction tomography imaging, and more particularly to a coil for magnetic induction tomography imaging.

BACKGROUND

Magnetic induction tomography imaging can be used to image an electromagnetic property distribution (e.g. conductivity or permittivity) within human tissues. More particularly, magnetic induction tomography techniques can provide for the low cost, contactless measurement of electromagnetic properties of human tissue based on eddy currents induced in tissues due to induction coils placed adjacent to the tissue.

Electromagnetic properties such as conductivity and permittivity vary spatially in human tissue due to natural contrasts created by fat, bone, muscle and various organs. As a result, a conductivity or permittivity distribution obtained using magnetic induction tomography imaging techniques can be used to image various regions of the body, including lungs and abdominal regions, brain tissue, and other regions of the body that may or may not be difficult to image using other low cost biomedical imaging techniques, such as ultrasound. In this way, magnetic induction tomography imaging can be useful in the biomedical imaging of, for instance, wounds, ulcers, brain traumas, and other abnormal tissue states.

Existing techniques for magnetic induction tomography imaging typically involve the placement of a large number of coils (e.g. a coil array) near the sample and building an image based upon the measured mutual inductance of coil pairs within the large number of coils placed near the specimen. For instance, an array of source coils and an array of detection coils can be placed adjacent the specimen. One or more of the source coils can be energized using radiofrequency energy and a response can be measured at the detection coils. The conductivity distribution (or permittivity distribution) of the specimen can be determined from the response of the detection coils.

SUMMARY

Aspects and advantages of embodiments of the present disclosure will be set forth in part in the following description, or may be learned from the description, or may be learned through practice of the embodiments.

One example aspect of the present disclosure is directed to a coil for magnetic induction tomography imaging of human tissue. The coil includes a plurality of first concentric conductive loops located within a first plane. The plurality of first concentric conductive loops are connected in series. The coil further includes a plurality of second concentric conductive loops located within a second plane. The second plane is spaced apart from the first plane by a plane separation distance. The plurality of second concentric conductive loops are connected in series. The plurality of first concentric conductive loops are connected in series with the plurality of second concentric loops. The plurality of first concentric conductive loops and the plurality of second concentric conductive loops are disposed such that each of the plurality of first concentric conductive loops overlaps one of the plurality of second concentric conductive loops.

Another example aspect of the present disclosure is directed to a method for providing a coil for magnetic induction tomography imaging. The method includes arranging a plurality of first concentric conductive loops in a first plane on a multilayer printed circuit board and arranging a plurality of second concentric conductive loops in a second plane on the multilayer printed circuit board. The method further comprises coupling the plurality of first concentric conductive loops in series using a plurality of first connection traces and coupling the plurality of second concentric conductive loops located in series using a plurality of second connection traces. The plurality of first connection traces and the plurality of second connection traces are radially aligned to connect the plurality of first concentric conductive loops and the plurality of second concentric conductive loops in series such that a current flow of one of the plurality of first connection traces is opposite a current flow of one of the plurality of second connection traces.

Yet another example aspect of the present disclosure is directed to a system for magnetic induction tomography imaging. The system includes an RF energy source and a coil coupled to the RF energy source. The coil includes a plurality of first concentric conductive loops located within a first plane. The plurality of first concentric conductive loops are connected in series with one another. The coil further includes a plurality of second concentric conductive loops located within a second plane. The plurality of second concentric conductive loops connected in series with one another. The system further includes a measurement circuit capable of obtaining a measurement of an electrical parameter of the coil when the coil is placed adjacent to a specimen. The first plane and the second plane are separated by a plane separation distance. The plane separation distance is selected such that the plurality of first concentric conductive loops and the plurality of second concentric conductive loops approximate a single plane of concentric conductive loops in a model used for magnetic induction tomography imaging.

Variations and modifications can be made to these example aspects of the present disclosure.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussions of embodiments directed to one of ordinary skill in the art are set forth in the specification, which makes reference to the appended figures, in which.

DETAILED DESCRIPTION

Figure 1:
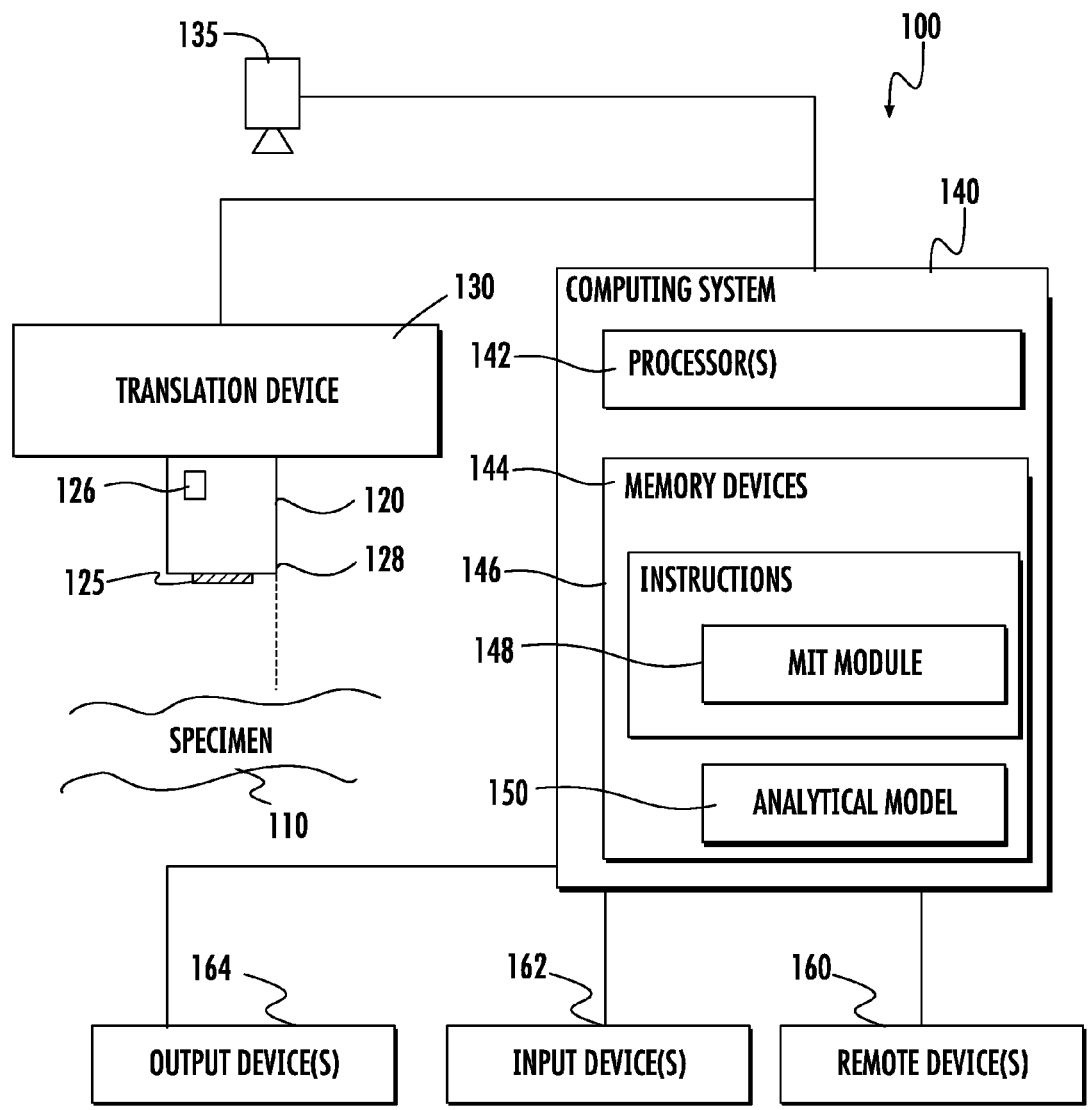
FIG. 1 depicts an example system for magnetic induction tomography imaging using a single coil according to example embodiments of the present disclosure.

Reference now will be made in detail to embodiments, one or more examples of which are illustrated in the drawings. Each example is provided by way of explanation of the embodiments, not limitation of the invention. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Overview

Generally, example aspects of the present disclosure are directed to a coil designed to facilitate magnetic induction tomography imaging of a specimen, such as a human tissue specimen, using a single coil. Typical existing magnetic induction tomography systems use a plurality of coils (e.g. an array of source coils and an array of detection coils) to generate conductivity maps of specimens, such as human tissue specimens. The use of multiple coils increases the complexity of magnetic induction tomography systems. For instance, multiplexing can be required to obtain measurements using the plurality of coils.

Efforts have been made to reduce the number of coils necessary for magnetic induction tomography imaging. For instance, fewer coils can be required by using techniques for repositioning the coils relative to the specimen or by repositioning the specimen relative to the coils. While it can be desirable to reduce the number of coils required for magnetic induction tomography imaging, it is still desirable to obtain as many measurements as possible to improve the resolution and accuracy of the images obtained using magnetic induction tomography.

A coil designed according to example aspects of the present disclosure can facilitate magnetic induction tomography imaging using a single coil. More particularly, the present inventors have discovered a model that defines the relationship between coil loss measurements obtained using a single coil and an electromagnetic property distribution of a specimen. In one implementation, the model is a quantitative analytical model that describes the real part of a change in impedance (e.g. ohmic loss) of a single planar multi-loop coil, having a plurality of concentric conductive loops, resulting from induced eddy currents when excited with RF energy and placed near to arbitrarily shaped objects with arbitrary three-dimensional conductivity distributions. A coil designed according to example aspects of the present disclosure, can approximate the single plane of concentric conductive loops provided for in the quantitative analytical model.

More particularly, the coil can include a plurality of concentric conductive circular loops with spacing sufficient between the loops, or sufficiently different radii, to reduce capacitive coupling with the specimen. The conductive loops can be connected in series with connection traces without allowing the connection traces to distort the fields produced by the plurality of concentric conductive circular loops. The plurality of concentric conductive loops can be arranged in multiple planes (e.g. on a multilayer printed circuit board) as a two layer stack. The spacing between the planes or the plane separation distance can be selected such that mathematically the plurality of conductive loops can be treated as being located in a common plane for purposes of the quantitative analytical model. For instance, the plane separation distance can be in the range of about 0.2 mm to about 0.7 mm, such as about 0.5 mm. As used herein, the use of the term "about" with reference to a dimension or other characteristic is intended to refer to within 20% of the specified dimension or other characteristic.

According to one particular example implementation of the present disclosure, the coil can include a plurality of first concentric conductive loops located within a first plane and a plurality of second concentric conductive loops located within a second plane. Each of the plurality of first conductive loops and each of the plurality of second conductive loops can include gaps (e.g. gaps about 0.5 mm or less) in the conductive loops to facilitate connecting the conductive loops in series. The plurality of gaps can be offset from one another to further facilitate connection of the plurality of conductive loops in series.

A plurality of connection traces can connect the conductive loops in series. For instance, a plurality of first connection traces can connect the first conductive loops in series and a plurality of second connection traces can connect the second conductive loops in series. The first and second connection traces can be arranged such that magnetic fields emanating from the connection traces oppose each other. For instance, one of the plurality of first connection traces can be nearly radially aligned with one of the plurality of second connection traces such that a current flow in the first connection trace is opposite a current flow in the second connection trace.

The coil designed according to example aspects of the present disclosure can be energized from an RF energy source (e.g. a 12.5 MHz RF energy source) coupled to the coil. For instance, an innermost conductive loop of the plurality of first conductive loops can be coupled to the RF energy source while an innermost conductive loop of the plurality of second conductive loops can be coupled to a reference node or electrical common. The magnetic field generated by the coil when energized by the RF energy source can behave as though it were sourced from a single plane of a plurality of concentric conductive loops.

Using the model, a three-dimensional electromagnetic property map can be generated for human tissue using a plurality of coil loss measurements obtained using the coil. More particularly, once a plurality of coil property measurements and associated position data for the coil loss measurements have been obtained, the measurements can be processed using the model to generate a three-dimensional map of the electromagnetic property distribution of the specimen, such as a three-dimensional conductivity map of the specimen.

Example Systems for Magnetic Induction Tomography Imaging

FIG. 1 depicts an example system 100 for magnetic induction tomography imaging of a specimen 110, such as a human tissue specimen. The system 100 includes a coil device 120 having a single coil 125 for obtaining coil property measurements for magnetic induction tomography imaging according to example aspects of the present disclosure. The coil 125 can be a single coil having a plurality of concentric conductive loops disposed in one or more planes on a printed circuit board. One example coil design for magnetic induction tomography imaging according to example aspects of the present disclosure will be discussed in more detail below with reference to FIGS. 4 and 5 below.

The coil device 120 of FIG. 1 can include an RF energy source (e.g. an oscillator circuit) configured to energize the coil 125 with RF energy at a set frequency (e.g. 12.5 MHz) when the coil 125 is placed adjacent to the specimen 110. The energized coil 125 can generate magnetic fields, which can induce eddy currents in the specimen 110. These induced eddy currents in the specimen can cause a coil loss (e.g. a change in impedance) of the coil 125. The coil device 120 can include circuitry (e.g. a measurement circuit) for determining the coil loss associated with the coil 125 during a coil property measurement at a particular location relative to the specimen 110.

Coil property measurements can be obtained using the single coil 125 of the coil device 120 while the coil device 120 is positioned at a variety of different locations and orientations relative to the specimen 110. The collected coil property measurements can be provided to the computing system 140 where the coil property measurements can be analyzed to generate a three-dimensional electromagnetic property map of the specimen 110, such as a three-dimensional conductivity map or a three-dimensional permittivity map of the specimen 110.

In some particular implementations, the coil device 120 can be mounted to a translation device 130. The translation device 130 can be a robotic device controlled, for instance, by the computing system 140 or other suitable control device, to translate the coil device 120 along x-, y-, and -z axes relative to the specimen 110 in order to position the coil 125 at a plurality of different discrete locations relative to the specimen 110. The coil device 120 can be controlled (e.g. by the computing system 140) to obtain a coil property measurement using the coil 125 at each of the plurality of discrete locations.

Alternatively, the coil device 120 can be manually positioned at the plurality of discrete locations for performance of the coil property measurement. For instance, a medical professional can manually position a hand held coil device 120 relative to the specimen 110 to obtain coil property measurements at a plurality of discrete locations relative to the specimen 110.

To generate an accurate three-dimensional electromagnetic property map of the specimen 110, position data needs to be associated with each of the obtained coil property measurements. The position data can be indicative of the position (e.g. as defined by an x-axis, y-axis, and a z-axis relative to the specimen 110) of the coil 125 as well as an orientation of the coil 125 (e.g. a tilt angle relative to the specimen 110). When using a translation device 130 to position the coil 125, the position and orientation of the coil 125 can be determined based at least in part on positioning control commands that control the translation device 130 to be positioned at the plurality of discrete locations.

In one embodiment of the present disclosure, images captured by a camera 135 positioned above the specimen 110 and the coil device 120 can be processed in conjunction with signals from various sensors associated with the coil device 120 to determine the position data for each coil property measurement. More particularly, the coil device 120 can include one or more motion sensors 126 (e.g. a three-axis accelerometer, gyroscope, and/or other motion sensors) and a depth sensor 128 The orientation of the single coil 125 relative to the surface can be determined using the signals from the motion sensors 126. For instance, signals from a three-axis accelerometer can be used to determine the orientation of the single coil 125 during a coil property measurement.

The depth sensor 128 can be used to determine the distance from the single coil to the specimen 110 (e.g. the position along the z-axis). The depth sensor 128 can include one or more devices configured to determine the location of the coil 125 relative to a surface. For instance, the depth sensor 128 can include one or more laser sensor devices and/or acoustic location sensors. In another implementation, the depth sensor 128 can include one or more cameras configured to capture images of the specimen 110. The images can be processed to determine depth to the specimen 110 using, for instance, structure-from-motion techniques.

Images captured by the camera 135 can be used to determine the position of the coil 125 along the x-axis and y-axis. More particularly, the coil device 120 can also include a graphic located on a surface of the coil device 120. As the plurality of coil property measurements are performed, the image capture device 135 can capture images of the graphic. The images can be provided to the computing system 140, which can process the images based on the location of the graphic to determine the position along the x-axis and y-axis relative to the specimen 110. In particular implementations, the camera 135 can include a telecentric lens to reduce error resulting from parallax effects.

The computing system 140 can receive the coil property measurements, together with coil location and orientation data, and can process the data to generate a three-dimensional electromagnetic property map of the specimen 110. The computing system 140 can include one or more computing devices, such as one or more of a desktop, laptop, server, mobile device, display with one or more processors, or other suitable computing device having one or more processors and one or more memory devices. The computing system 140 can be implemented using one or more networked computers (e.g., in a cluster or other distributed computing system). For instance, the computing system 140 can be in communication with one or more remote devices 160 (e.g. over a wired or wireless connection or network).

The computing system 140 includes one or more processors 142 and one or more memory devices 144. The one or more processors 142 can include any suitable processing device, such as a microprocessor, microcontroller, integrated circuit or other suitable processing device. The memory devices 144 can include single or multiple portions of one or more varieties of tangible, non-transitory computer-readable media, including, but not limited to, RAM, ROM, hard drives, flash drives, optical media, magnetic media or other memory devices. The computing system 140 can further include one or more input devices 162 (e.g. keyboard, mouse, touchscreen, touchpad, microphone, etc.) and one or more output devices 164 (e.g. display, speakers, etc.).

The memory devices 144 can store instructions 146 that when executed by the one or more processors 142 cause the one or more processors 142 to perform operations. The computing device 140 can be adapted to function as a special-purpose machine providing desired functionality by accessing the instructions 146. The instructions 146 can be implemented in hardware or in software. When software is used, any suitable programming, scripting, or other type of language or combinations of languages may be used to implement the teachings contained herein.

As illustrated, the memory devices 144 can store instructions 146 that when executed by the one or more processors 142 cause the one or more processors 142 to implement a magnetic induction tomography ("MIT") module 148. The MIT module 148 can be configured to implement one or more of the methods disclosed herein for magnetic induction tomography imaging using a single coil, such as the method disclosed in FIG. 8.

The one or more memory devices 144 of FIG. 1 can also store data, such as coil property measurements, position data, three-dimensional electromagnetic property maps, and other data. As shown, the one or more memory devices 144 can store data associated with an analytical model 150. The analytical model 150 can define a relationship between coil property measurements obtained by a single coil and an electromagnetic property distribution of the specimen 110. Features of an example analytical model will be discussed in more detail below.

MIT module 148 may be configured to receive input data from input device 162, from coil device 120, from translation device 130, from data that is stored in the one or more memory devices 144, or other sources. The MIT module 148 can then analyze such data in accordance with the disclosed methods, and provide useable output such as three-dimensional electromagnetic property maps to a user via output device 164. Analysis may alternatively be implemented by one or more remote device(s) 160.

The technology discussed herein makes reference to computing systems, servers, databases, software applications, and other computer-based systems, as well as actions taken and information sent to and from such systems. One of ordinary skill in the art, using the disclosures provided herein, will recognize that the inherent flexibility of computer-based systems allows for a great variety of possible configurations, combinations, and divisions of tasks and functionality between and among components. For instance, processes discussed herein may be implemented using a single computing device or multiple computing devices working in combination. Databases and applications may be implemented on a single system or distributed across multiple systems. Distributed components may operate sequentially or in parallel.

Figure 2:
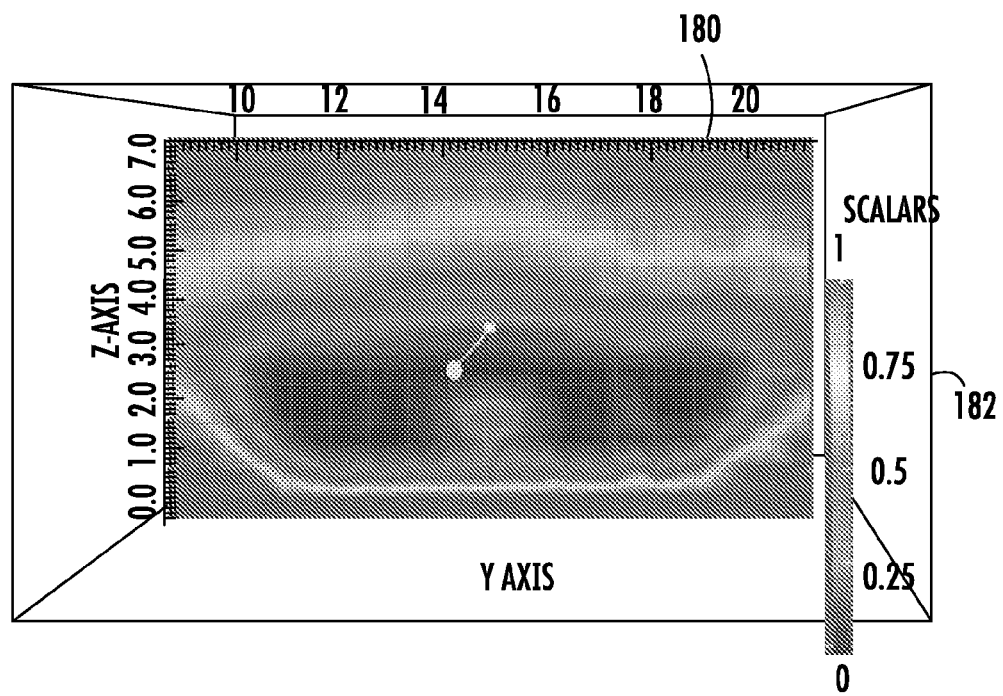
FIGS. 2-3 depict example conductivity maps generated according to example embodiments of the present disclosure.

FIG. 2 depicts one example conductivity map 180 that can be generated by the system 100 from a plurality of coil property measurements using a single coil according to an example embodiment of the present disclosure. The conductivity map 180 can provide a two-dimensional view of a cross-section of a three-dimensional conductivity map generated by the MIT module 148 of FIG. 1 based on measurements obtained by the coil device 120. The conductivity map 180 of FIG. 2 can be presented, for instance, on the output device 164 of the computing system 140 of FIG. 1.

The conductivity map 180 of FIG. 2 provides a transverse view of a spinal column of a patient, transecting and revealing the spinal canal. The conductivity map 180 plots conductivity distribution along x-, y-, and z-axes in units of centimeters. The conductivity map 180 includes a scale 182 indicative of grey scale colors associated with varying degrees of conductivity in units of S/m. As shown, the conductivity map 180 shows the contrasting conductivity of regions of human tissue in the spinal region and can provide an image of the spinal region of the patient.

Figure 3:
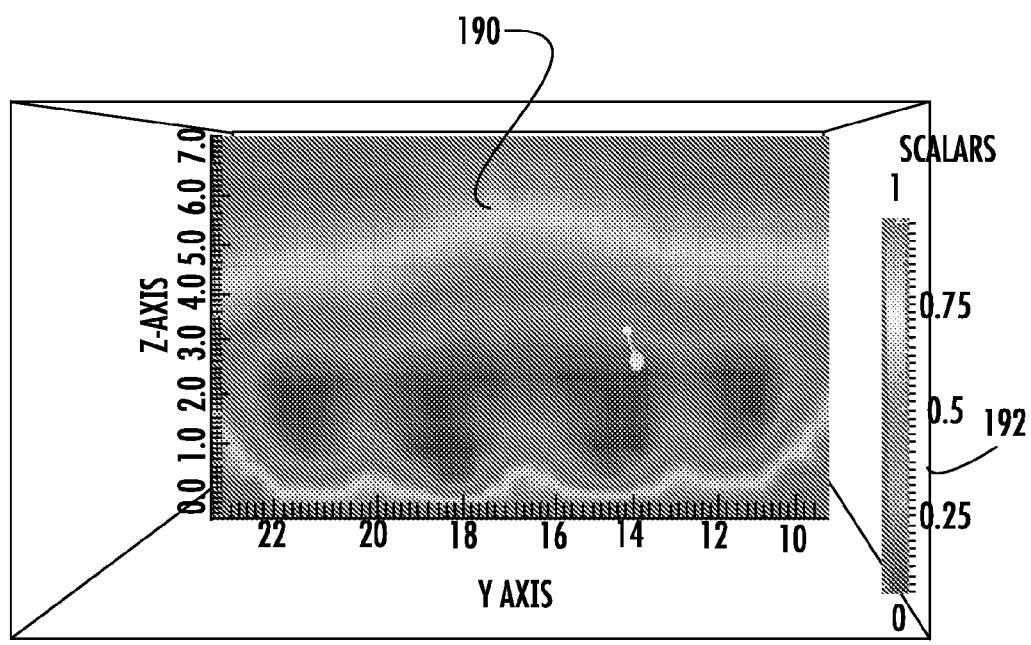

FIG. 3 depicts another example conductivity map 190 that can be generated by the system 100 from a plurality of coil property measurements using a single coil according to example embodiments of the present disclosure. The conductivity map 190 can be a two-dimensional view of a cross-section of a three-dimensional conductivity map generated by the MIT module 148 of FIG. 1 based on measurements obtained by the coil device 120. The conductivity map 190 of FIG. 3 can be presented, for instance, on the output device 164 of the computing system 140 of FIG. 1.

The conductivity map 190 of FIG. 3 provides a sagittal view of the spinal region of a patient, offset but parallel to the spinal column. The conductivity map 190 plots conductivity distribution along x-, y-, and z-axes in units of centimeters. The conductivity map 190 includes a scale 192 indicative of grey scale colors associated with varying degrees of conductivity, in units of S/m. As shown, the conductivity map 190 shows the contrasting conductivity of regions of human tissue in the spinal region and can provide an image of the spinal region of the patient. This slice transects and reveals the structure associated with the connection of ribs to transverse processes of the vertebrae. The conductivity map 180 and the conductivity map 190, together with other views, can provide varying images of the spinal region of the patient for diagnostic and other purposes.

Example Quantitative Analytical Model for a Single Coil

An example quantitative analytical model for obtaining a three-dimensional conductivity map from a plurality of coil property measurements obtained by a single coil will now be set forth. The quantitative model is developed for an arbitrary conductivity distribution, but with permittivity and magnetic permeability treated as spatially uniform. The quantitative analytical model was developed for a coil geometry that includes a plurality of concentric circular loops, all lying within a common plane and connected in series, with the transient current considered to have the same value at all points along the loops. A conductivity distribution is permitted to vary arbitrarily in space while a solution for the electric field is pursued with a limit of small conductivity (<10 S/m). Charge free conditions are assumed to hold, whereby the electrical field is considered to have zero divergence. Under these conditions, fields are due only to external and eddy currents.

The quantitative analytical model can correlate a change in the real part of impedance (e.g. ohmic loss) of the coil with various parameters, including the conductivity distribution of the specimen, the position and orientation of the single coil relative to the specimen, coil geometry (e.g. the radius of each of the plurality of concentric conductive loops) and other parameters. One example model is provided below:

$$-\delta Z_{re} = \frac{\mu^2 \omega^2}{4\pi^2} \sum_{j,k} \sqrt{\rho_j \rho_k} \int d^3x \frac{\bar{\sigma}(\bar{r})}{\rho} Q_{\frac{1}{2}}(\eta_j) Q_{\frac{1}{2}}(\eta_k)$$

$-\delta Z_{re}$ is the coil property measurement (e.g. the real part of the impedance loss of the coil). μ is the magnetic permeability in free space. ω is the excitation frequency of the coil. $\rho_k$ and $\rho_j$ are the radii of each conductive loop j and k for each interacting loop pair j,k. The function $Q_{1/2}$ is known as a ring function or toroidal harmonic function, which has the argument $\eta_j$ and $\eta_k$ as shown here:

$$\eta_j = \frac{\rho^2 + \rho_j^2 + z^2}{2\rho\rho_j}$$

$$\eta_k = \frac{\rho^2 + \rho_k^2 + z^2}{2\rho\rho_k}$$

With reference to a coordinate system placed at the center of the concentric loops, such that loops all lie within the XY-plane, $\rho$ measures radial distance from coil axis to a point within the specimen while z measures distance from the coil plane to the same point within the specimen.

The model introduces electrical conductivity $\check{\sigma}(\vec{r})$ as a function of position. The integrals can be evaluated using a finite element mesh (e.g. with tetrahedral elements) to generate the conductivity distribution for a plurality of coil property measurements as will be discussed in more detail below.

Example Coil Device for Magnetic Induction Tomography Imaging

As demonstrated above, the inventors have developed a quantitative analytical model that defines a relationship between a plurality of coil property measurements obtained by a single coil having a plurality of concentric conductive loops connected in series and a conductivity distribution of a specimen. An example coil design that approximates the coil contemplated by the example quantitative model will now be set forth A coil according to example aspects of the present disclosure can include a plurality of concentric conductive loops arranged in two-planes on a multilayer printed circuit board. The plurality of concentric conductive loops can include a plurality of first concentric conductive loops located within a first plane and a plurality of second concentric conductive loops located in a second plane. The second plane can be spaced apart from the first plane by a plane separation distance. The plane separation distance can be selected such that the coil approximates the single plane coil contemplated in the example quantitative analytical model for magnetic induction tomography imaging disclosed herein.

In addition, the plurality of conductive loops can be connected in series using a plurality of connection traces. The plurality of connection traces can be arranged so that the contribution to the fields generated by the connection traces can be reduced. In this manner, the coil according to example aspects of the present disclosure can exhibit behavior that approximates a plurality of circular loops arranged concentric to one another and located in the same plane.

Figure 4:
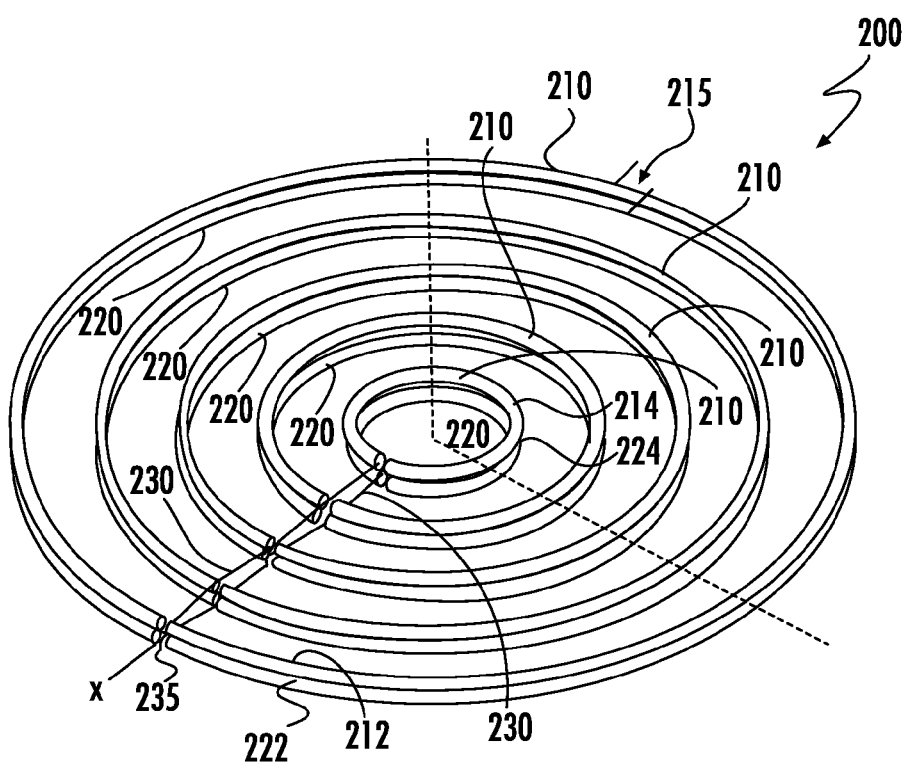
FIG. 4 depicts an example coil for magnetic induction tomography imaging according to example embodiments of the present disclosure.

FIG. 4 depicts an example coil 200 used for magnetic induction tomography imaging according to example aspects of the present disclosure. As shown, the coil 200 includes ten concentric conductive loops. More particularly, the coil 200 includes five first concentric conductive loops 210 disposed in a first plane and five second concentric conductive loops 220 disposed in a second plane. The first and second concentric conductive loops 210 and 220 can be 1 mm or 0.5 mm copper traces on a multilayer printed circuit board. In one example implementation, the radii of the five concentric conductive loops in either plane are set at about 4 mm, 8 mm, 12 mm, 16 mm, and 20 mm respectively. Other suitable dimensions and spacing can be used without deviating from the scope of the present disclosure.

As shown, each of the plurality of first concentric conductive loops 210 is disposed such that it overlaps one of the plurality of second concentric conductive loops 220. In addition, the first concentric conductive loops 210 and the second concentric conductive loops 220 can be separated by a plane separation distance. The plane separation distance can be selected such that the coil 200 approximates a single plane of concentric coils as contemplated by the quantitative analytical model. For instance, the plane separation distance can be in the range of about 0.2 mm to about 0.7 mm, such as about 0.5 mm.

The plurality of first conductive loops 210 can include a first innermost conductive loop 214. The first innermost conductive loop 214 can be coupled to an RF energy source. The plurality of second conductive loops 220 can include a second innermost conductive loop 224. The second innermost conductive loop 224 can be coupled to a reference node (e.g. a ground node or common node).

The coil further includes a plurality of connection traces 230 that are used to connect the first concentric conductive loops 210 and the second concentric conductive loops 220 in series. More particularly, the connection traces 230 couple the plurality of first concentric conductive loops 210 in series with one another and can couple the plurality of second concentric conductive loops 220 in series with one another. The connection traces 230 can also include a connection trace 235 that couples the outermost first concentric conductive loop 212 with the outermost second concentric conductive loop 214 in series.

Figure 5:
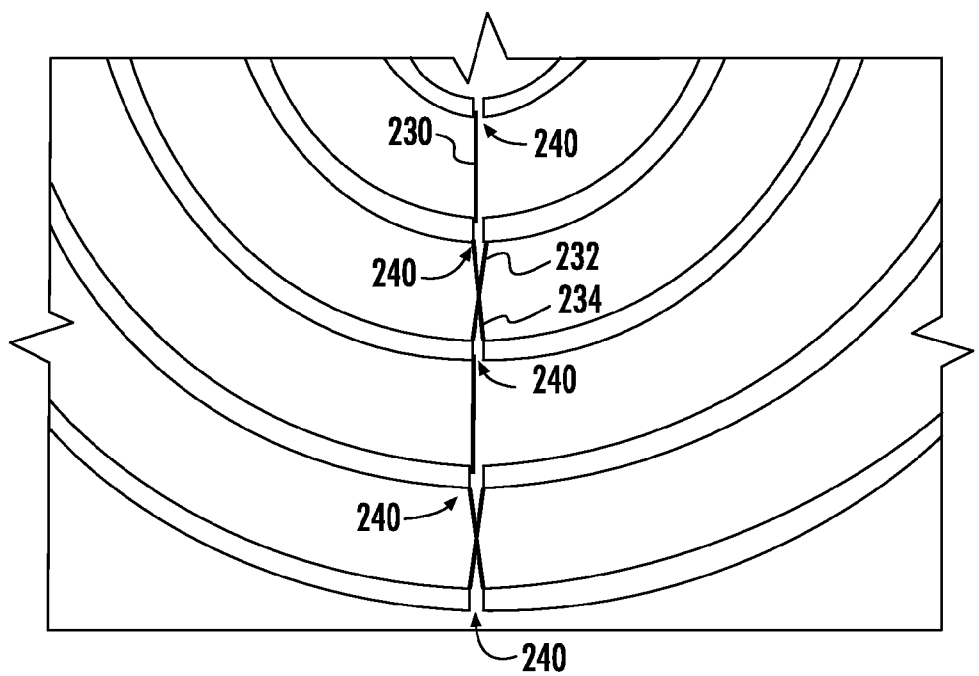
FIG. 5 depicts example connection traces for a coil for magnetic induction tomography imaging according to example embodiments of the present disclosure.

As shown in more detail in FIG. 5, the connection traces 230 can be arranged such that fields emanating from the connection traces oppose each other. More particularly, the connection traces 230 can be radially aligned such that a current flow of one of the plurality of connection traces located in the first plane is opposite to a current flow of one of the plurality of connection traces located in the second plane. For instance, referring to FIG. 5, connection trace 232 arranged in the first plane can be nearly radially aligned with connection trace 234 in the second plane. A current flowing in connection trace 232 can be opposite to the current flowing in connection trace 234 such that fields generated by the connection traces 232 and 234 oppose or cancel each other.

As further illustrated in FIG. 5, each of the plurality of first conductive loops 210 and the second conductive loops 220 can include a gap 240 to facilitate connection of the conductive loops using the connection traces 230. The gap can be in the range of about 0.2 mm to about 0.7 mm, such as about 0.5 mm.

The gaps 240 can be offset from one another to facilitate connection of the plurality of concentric conductive loops 210 and 220 in series. For instance, a gap associated with one of the plurality of first concentric conductive loops 210 can be offset from a gap associated with another of the plurality of first concentric conductive loops 210. Similarly, a gap associated with one of the plurality of second concentric conductive loops 220 can be offset from a gap associated with another of the plurality of second concentric conductive loops 220. A gap associated with one of the first concentric conductive loops 210 can also be offset from a gap associated with one of the plurality of second concentric conductive loops 220. Gaps that are offset may not be along the same axis associated with the coil 200.

As shown in the experimental results that follow, the coil 200 of FIGS. 4 and 5 can provide a good approximation of the coil contemplated by the quantitative analytical model for magnetic induction tomography imaging. In this way, coil property measurements using the coil 200 can be used to generate three-dimensional electromagnetic property maps of specimens of interest (e.g. human tissue specimens).

Figure 6:
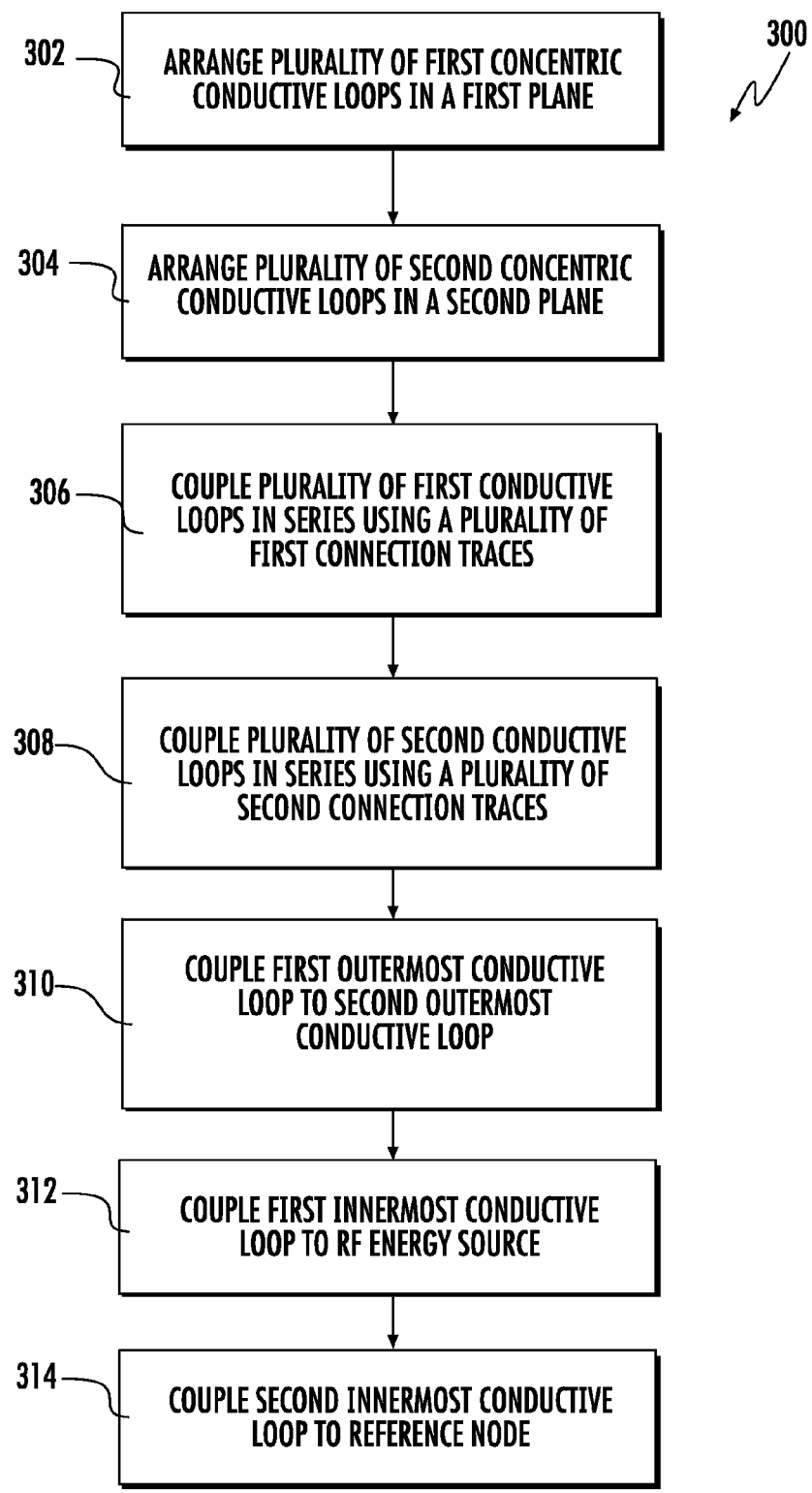
FIG. 6 depicts a process flow diagram of an example method for providing a coil for magnetic induction tomography imaging according to example embodiments of the present disclosure.

FIG. 6 depicts a process flow diagram of an example method (300) for providing a coil for magnetic induction tomography imaging according to example aspects of the present disclosure. FIG. 6 depicts steps performed in a particular order for purposes of illustration and discussion. Those of ordinary skill in the art, using the disclosures provided herein, will understand that the steps of any of the methods disclosed herein can be modified, omitted, rearranged, adapted, or expanded in various ways without deviating from the scope of the present disclosure.

At (302), a plurality of first concentric conductive loops are arranged in a first plane. For instance, the plurality of first concentric conductive loops 210 of the coil 200 of FIG. 4 are arranged on a first plane of a multilayer printed circuit board. At (304) of FIG. 6, a plurality of second concentric conductive loops are arranged in a second plane. For instance, the plurality of second concentric conductive loops 220 of FIG. 4 are arranged on a second plane of a multilayer printed circuit board.

The first plane and the second plane can be separated by a plane separation distance. The plane separation distance can be selected such that the coil approximates a single plane of concentric conductive loops in the analytical model for magnetic induction tomography disclosed herein. For instance, the plane separation distance can be selected to be in the range of 0.2 mm to 0.7 mm.

At (306), the plurality of first concentric conductive loops are coupled in series using a plurality of first connection traces in the first plane. At (308) of FIG. 6, the plurality of second concentric conductive loops are coupled in series using a plurality of second connection traces in the second plane. The connection traces can be radially aligned such that fields generated by the connection traces oppose each other. For instance, the connection traces can be arranged such that the plurality of first connection traces and the plurality of second connection traces are radially aligned to connect the plurality of first concentric conductive loops and the plurality of second concentric conductive loops in series such that a current flow of one of the plurality of first connection traces is opposite a current flow of one of the plurality of second connection traces.

At (308), the method can include coupling a first outermost conductive loop located in the first plane with a second outermost conductive loop in the second plane such that the plurality of first concentric conductive loops and the plurality of second concentric conductive loops are coupled in series. For instance, referring to FIG. 4, first outermost conductive loop 212 can be coupled in series with the second outermost conductive loop 222.

At (310) of FIG. 6, the method can include coupling a first innermost conductive loop to an RF energy source. For instance, referring to FIG. 4, an innermost conductive loop 214 of the plurality of first concentric conductive loops 210 can be coupled to an RF energy source. At (312) of FIG. 6, a second innermost conductive loop can be coupled to a reference node (e.g. a ground node or a common node). For instance, referring to FIG. 4, an innermost conductive loop 224 of the plurality of second concentric conductive loops 220 can be coupled to a reference node.

Example Circuit for Obtaining Coil Property Measurements

Figure 7:
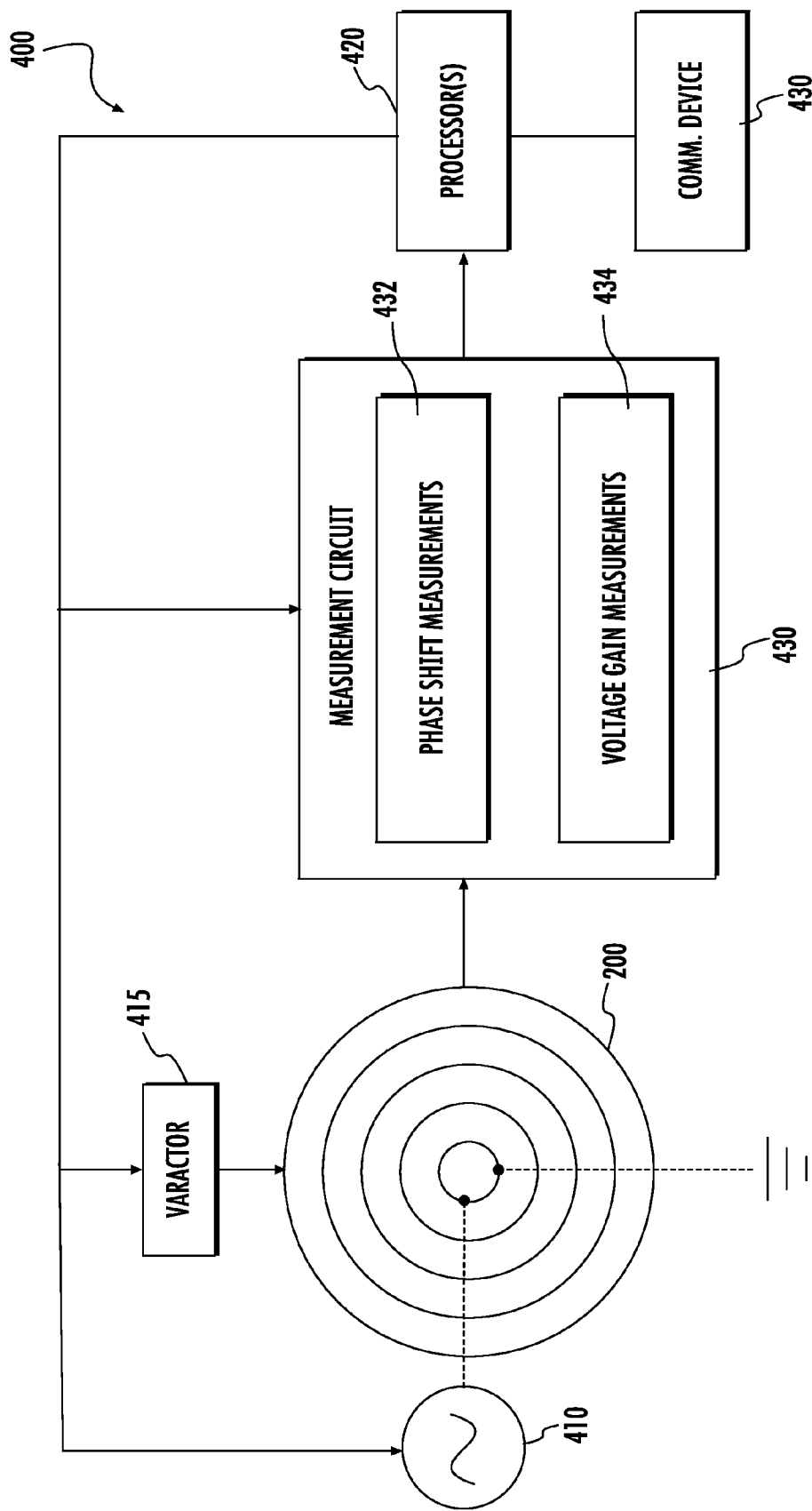
FIG. 7 depicts a block diagram of an example circuit associated with a coil used for magnetic induction tomography imaging according to example embodiments of the present disclosure.

FIG. 7 depicts a diagram of an example circuit 400 that can be used to obtain coil property measurements using the coil 200 of FIGS. 4 and 5. As shown, the circuit 400 of FIG. 7 includes an RF energy source 410 (e.g. an oscillator circuit) configured to energize the coil 200 with RF energy. The RF energy source 410 can be a fixed frequency crystal oscillator configured to apply RF energy at a fixed frequency to the coil 200. The fixed frequency can be, for instance, about 12.5 MHz. In one example embodiment, the RF energy source 410 can be coupled to an innermost concentric conductive loop of the plurality of first concentric conductive loops of the coil 200. The innermost concentric conductive loop of the plurality of second concentric conductive loops of the coil 200 can be coupled to a reference node (e.g. common or ground).

The circuit 400 can include one or more processors 420 to control various aspects of the circuit 400 as well as to process information obtained by the circuit 400 (e.g. information obtained by measurement circuit 430). The one or more processors 420 can include any suitable processing device, such as digital signal processor, microprocessor, microcontroller, integrated circuit or other suitable processing device.

The one or more processors 420 can be configured to control various components of the circuit 400 in order to capture a coil loss measurement using the coil 200. For instance, the one or more processors 420 can control a varactor 415 coupled in parallel with the coil 200 so as to drive the coil 200 to resonance or near resonance when the coil 200 is positioned adjacent a specimen for a coil property measurement. The one or more processors 420 can also control the measurement circuit 430 to obtain a coil property measurement when the coil 200 is positioned adjacent the specimen.

The measurement circuit 430 can be configured to obtain coil property measurements with the coil 200. The coil property measurements can be indicative of coil losses of the coil 200 resulting from eddy currents induced in the specimen. In one implementation, the measurement circuit 430 can be configured to measure the real part of admittance changes of the coil 200. The real part of admittance changes of the coil 200 can be converted to real part of impedance changes of the coil 200 as the inverse of admittance for purposes of the analytical model.

The admittance of the coil 200 can be measured in a variety of ways. In one embodiment, the measurement circuit 430 measures the admittance using a phase shift measurement circuit 432 and a voltage gain measurement circuit 434. For instance, the measurement circuit 430 can include an AD8302 phase and gain detector from Analog Devices. The phase shift measurement circuit 432 can measure the phase shift between current and voltage associated with the coil 200. The voltage gain measurement circuit 434 can measure the ratio of the voltage across the coil 200 with a voltage of a sense resistor coupled in series with the coil 200. The admittance of the coil 200 can be derived (e.g. by the one or more processors 420) based on the phase and gain of the coil 200 as obtained by the measurement circuit 430.

Once the coil property measurements have been obtained, the one or more processors 420 can store the coil property measurements, for instance, in a memory device. The one or more processors 420 can also communicate the coil property measurements to one or more remote devices for processing to generate a three-dimensional electromagnetic property map of the specimen using communication device 440. Communication device 440 can include any suitable interface or device for communicating information to a remote device over wired or wireless connections and/or networks.

Example Methods for Magnetic Induction Tomography Imaging

Figure 8:
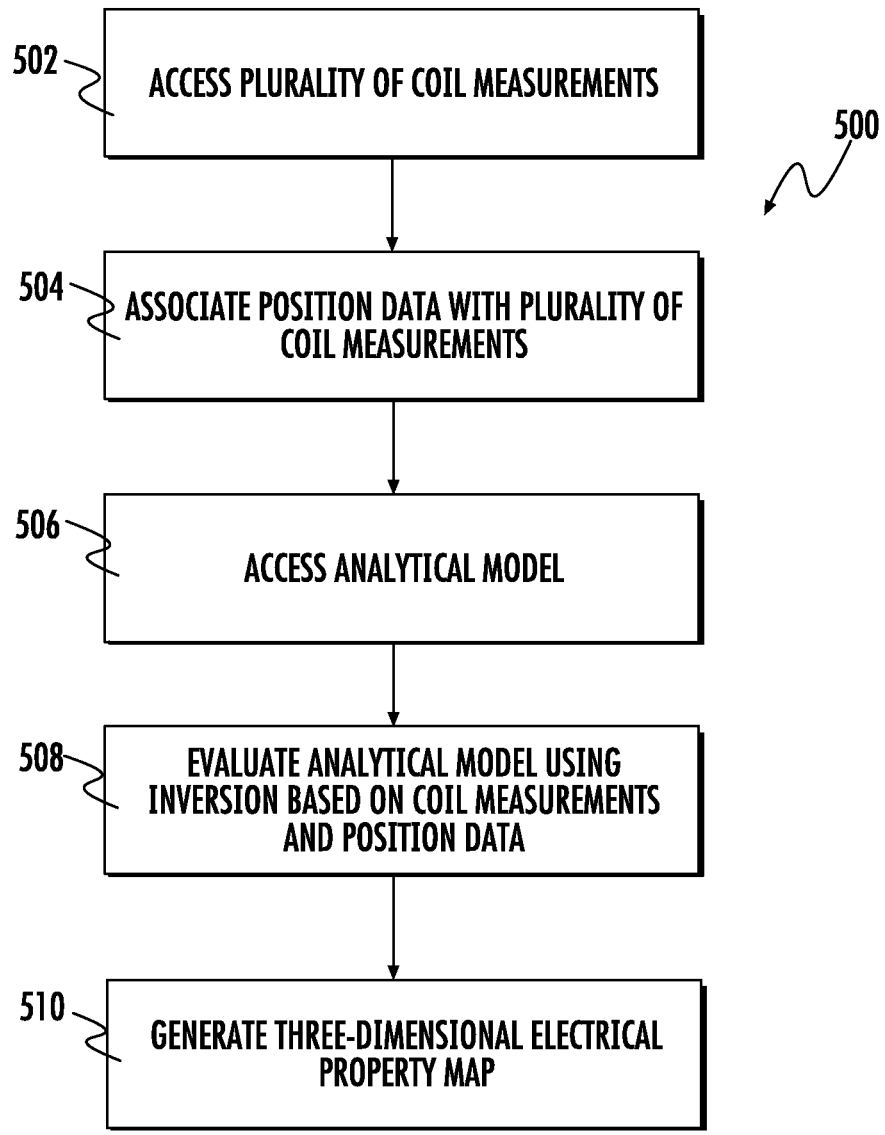
FIG. 8 depicts a process flow diagram of an example method for magnetic induction tomography imaging according to example embodiments of the present disclosure.

FIG. 8 depicts a process flow diagram of an example method (500) for magnetic induction tomography imaging according to example aspects of the present disclosure. The method (500) can be implemented by one or more computing devices, such as one or more computing devices of the computing system 140 depicted in FIG. 1. In addition, FIG. 8 depicts steps performed in a particular order for purposes of illustration and discussion. Those of ordinary skill in the art, using the disclosures provided herein, will understand that the steps of any of the methods disclosed herein can be modified, omitted, rearranged, adapted, or expanded in various ways without deviating from the scope of the present disclosure.

At (502), the method can include accessing a plurality of coil property measurements obtained using a single coil at a plurality of different discrete locations relative to the specimen. For instance, the plurality of coil property measurements can be accessed from a memory device or can be received from a coil device having a single coil configured for obtaining the coil property measurements. The coil property measurements can be coil loss measurements captured by a single coil when the single coil is energized with RF energy and placed adjacent a specimen at one of the plurality of discrete locations.

In one implementation, the single coil can include a plurality of concentric conductive loops. For instance, the single coil can have a plurality of first concentric conductive loops arranged in a first plane and a plurality of second concentric conductive loops arranged in a second plane. The plurality of concentric conductive loops can be connected using connection traces arranged so as to have a reduced impact on the field created by the coil. For example, the single coil can have the coil geometry of the coil 200 depicted in FIGS. 4 and 5.

The coil property measurements can be obtained at a plurality of discrete positions relative to the specimen. Each coil property measurement can be taken at a different discrete position relative to the specimen. A greater number of coil property measurements can lead to increased accuracy in generating a three-dimensional electromagnetic property map from the coil property measurements.

In a particular embodiment, the coil property measurements can include a plurality of different data sets of coil property measurements. Each of the data sets can be built by conducting a plurality of coil property measurements using a single coil. The single coil can be different for each data set. For instance, each data set can be associated with a single coil having a different overall size and/or outer diameter, relative to any of the other single coils associated with the other data sets. The data sets can be obtained at different times. The data sets can be collectively processed according to example aspects of the present disclosure to generate a three-dimensional electrical property distribution of the specimen as discussed below.

At (504) of FIG. 8, the method includes associating position data with each of the plurality of coil property measurements. The position data for each coil property measurement can be indicative of the position and orientation of the single coil relative to the specimen when the coil property measurement was performed. The position data can be associated with each coil property measurement, for instance, in a memory device of a computing system.

The position data can be obtained in a variety of ways. In one implementation, the position data can be obtained for each measurement from data associated with a translation device used to position the single coil relative to the specimen at the plurality of discrete locations relative to the specimen. For example, the translation device can be controlled to position the single coil at a plurality of defined locations relative to the specimen. The position data can be determined from these defined locations.

Signals from one or more sensors (e.g. one or more motion sensors and one or more depth sensors) associated with the single coil can be also used to determine the position data for a coil property measurement. Images can also be captured of the coil device containing the single coil as the plurality of coil property measurements is performed. The position of the single coil can be determined for instance, based on the position of a graphic on the surface of the coil device depicted in the images.

At (506), the method includes accessing an analytical model defining a relationship between coil property measurements obtained by the single coil and an electromagnetic property of the specimen. For instance, the analytical model can be accessed, for instance, from a memory device. In one particular implementation, the analytical model correlates a change in impedance of single coil having a plurality of concentric conductive loops with a conductivity distribution of the specimen. More particularly, the analytical model can correlate the change in impedance of a single coil with a variety of parameters. The parameters can include the conductivity distribution of the specimen, the position and orientation associated with each coil loss measurement, and the geometry of the coil (e.g. the radius of each of the concentric conductive loops). Details concerning an example quantitative model were provided in the discussion of the example quantitative analytical model for a single coil discussed above.

At (508), the method includes evaluating the analytical model based on the plurality of coil property measurements and associated position data. More particularly, an inversion can be performed using the model to determine a conductivity distribution that most closely leads to the plurality of obtained coil property measurements. In one example aspect, the inversion can be performed by discretizing the specimen into a finite element mesh. The finite element mesh can include a plurality of polygonal elements, such as tetrahedral elements. The shape and resolution of the finite element mesh can be tailored to the specimen being analyzed. As a matter of practicality, the coil location data can be used to avoid meshing those regions of space visited by the coil, improving efficiency. Once the finite element mesh has been generated for the specimen, a conductivity distribution for the finite element mesh can be computed using a non-linear or constrained least squares solver.

More particularly, a plurality of candidate electromagnetic property distributions can be computed for the finite element mesh. Each of these candidate electromagnetic property distributions can be evaluated using a cost or objective function, such as the root mean square error. The cost or objective function can assign a cost to each candidate electromagnetic property distribution based at least in part on the difference between the obtained coil property measurements and theoretical coil property measurements using the model. The candidate electromagnetic property distribution with the lowest cost can be selected as the electromagnetic property distribution for the specimen. Those of ordinary skill in the art, using the disclosures provided herein, will understand that other suitable techniques can be used to determine an electromagnetic property distribution using the analytical model without deviating from the scope of the present disclosure.

At (510), a three-dimensional electromagnetic property map can be generated based on the electromagnetic property distribution identified using the inversion algorithm. The three-dimensional property map can provide an electromagnetic property distribution (e.g. a conductivity distribution) for a plurality of three-dimensional points associated with the specimen. Two-dimensional views along cross-sections of the three-dimensional electromagnetic property map can then be captured and presented, for instance, on a display device. Three-dimensional views of the electromagnetic property map can also be generated, rotated, and presented, for instance, on a display device.

Experimental Results #1

Two coils having a coil geometry of the coil 200 depicted in FIGS. 4 and 5 were constructed. Coil "R" had a 1 mm trace width. Coil "S" had a 0.5 mm trace width. Each trace was built with 2 oz. copper. The traces on coil "R" had an equivalent circular wire diameter of 0.68 mm, equivalent in the sense of having identical perimeters. The traces on coil "S" had an equivalent circular wire diameter of 0.36 mm.

The coil was positioned at a plurality of discrete locations relative to a specimen including a 30 cm×30 cm×13 cm deep tank of aqueous KCl having known conductivity. Admittance change relative to free space was measured and then used to compute loss. This was then compared to theoretical losses computed using the quantitative analytical model discussed above.

Figure 9:
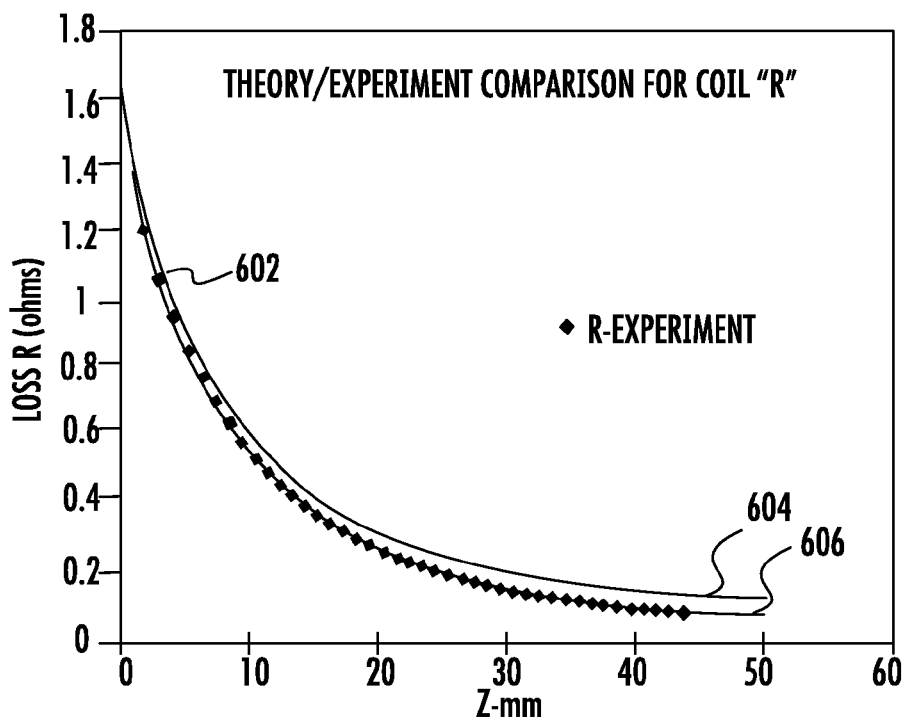
FIGS. 9 and 10 depict experimental results for coil property measurements obtained using an example according to example embodiments of the present disclosure.

FIG. 9 depicts a comparison of theoretical losses versus observed losses for coil "R". FIG. 9 plots depth from, or distance above, the specimen along the abscissa and coil losses along the ordinate. Curve 602 depicts the observed losses for coil "R". Curve 604 depicts theoretical losses for an infinite slab 13 cm thick. Curve 606 depicts theoretical losses for a finite slab.

Figure 10:
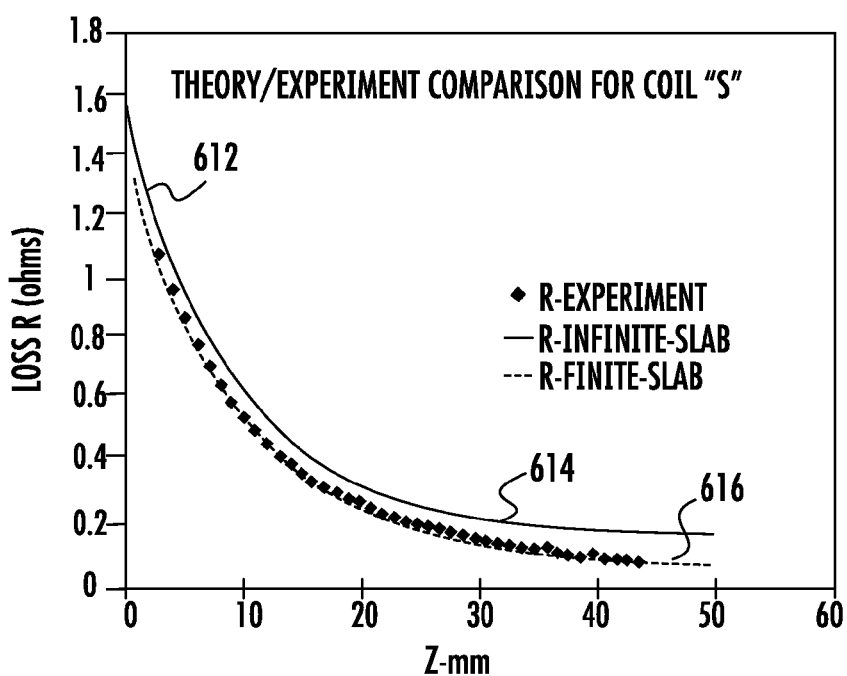

FIG. 10 depicts a comparison of theoretical losses versus observed losses for coil "S". FIG. 10 plots depth from, or distance above, the specimen along the abscissa and coil losses along the ordinate. Curve 612 depicts the observed losses for coil "S". Curve 614 depicts theoretical losses for an infinite slab 13 cm thick. Curve 616 depicts theoretical losses for a finite slab.

As demonstrated in FIGS. 9 and 10, coil property measurements obtained using the coil geometry of the coil 200 of FIGS. 4 and 5 closely track theoretical ohmic losses using the example quantitative analytical model disclosed herein. As a result the coil 200 of FIGS. 4 and 5 can be effectively used for magnetic induction tomography imaging using a single coil according to example aspects of the present disclosure.

Experimental Results #2

To test the example quantitative analytical model according to example aspects of the preset disclosure, a specimen including slab with dimensions 9 cm×9 cm square and 2 cm thick was subdivided into two layers. A finite element mesh was generated for the specimen consisting of 380 pentahedral elements and 342 nodes. Electrical conductivity is distributed over the mesh nodes varying in conductivity from 1.0 S/m near the corners to 3.0 S/m near the center. FIG. 10 shows the theoretical conductivity distribution 620 defined for the specimen according to the following:

$$\check{\sigma}(x, y) = 1 + \sin^2\left(\frac{x}{3}\right) + \sin^2\left(\frac{y}{3}\right)$$

Figure 11:
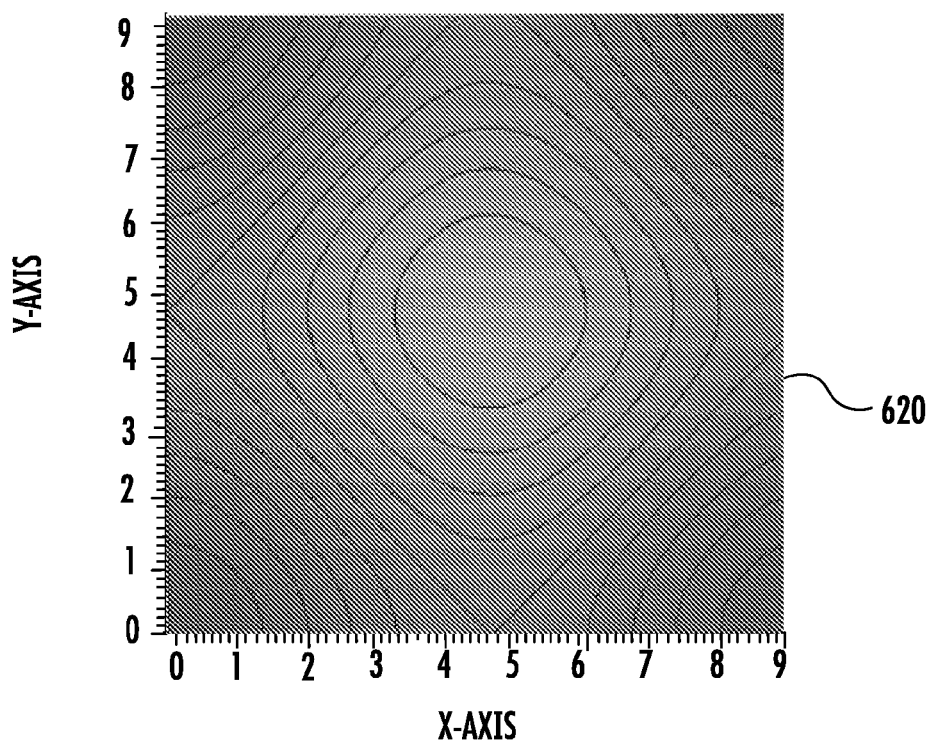
FIGS. 11 and 12 depict experimental results for coil property measurements obtained for a simulated conductivity distribution according to example embodiments of the present disclosure.
Figure 12:
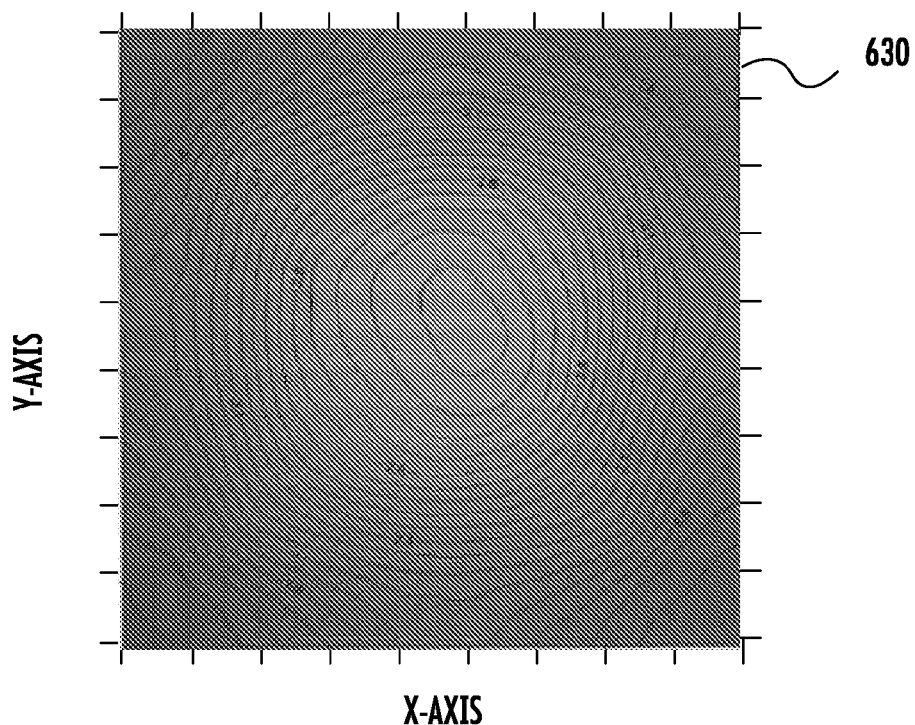

Nine virtual coil property measurements were simulated using a single coil at nine discrete coil positions. An inversion was performed using the quantitative analytical model based at least in part on the nine coil property measurements. FIG. 11 depicts the resulting three-dimensional conductivity map 630 determined using the inversion. As demonstrated, the three-dimensional conductivity map 630 approximates the true conductivity distribution 620 and is determined using only nine coil property measurements by a single coil at discrete positions relative to the specimen.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A coil for magnetic induction tomography imaging of a specimen, comprising:
    a plurality of first concentric conductive loops located within a first plane, the plurality of first concentric conductive loops connected in series; and
    a plurality of second concentric conductive loops located within a second plane, the second plane spaced apart from the first plane by a plane separation distance, the plurality of second concentric conductive loops connected in series;
    wherein the plurality of first concentric conductive loops are connected in series with the plurality of second concentric conductive loops, the plurality of first concentric conductive loops and the plurality of second concentric conductive loops being disposed such that each of the plurality of first concentric conductive loops overlaps one of the plurality of second concentric conductive loops.

2. The coil of claim 1, wherein the plane separation distance is selected such that the plurality of first concentric conductive loops and the plurality of second concentric conductive loops approximate a single plane of concentric conductive loops in a model used for magnetic induction tomography imaging.

3. The coil of claim 1, wherein the plane separation distance is in the range of 0.2 mm to 0.7 mm.

4. The coil of claim 1, wherein the plurality of first concentric conductive loops and the plurality of second concentric conductive loops are connected in series using a plurality of connection traces.

5. The coil of claim 4, wherein the plurality of connection traces are arranged such that fields emanating from the connection traces oppose each other.

6. The coil of claim 4, wherein the plurality of connection traces are radially aligned to connect the plurality of first concentric conductive loops and the plurality of second concentric conductive loops in series such that a current flow of one of the plurality of connection traces located in the first plane is opposite a current flow of one of the plurality of connection traces located in the second plane.

7. The coil of claim 1, wherein each of the plurality of first concentric conductive loops has a gap to facilitate series connection of the plurality of first concentric conductive loops.

8. The coil of claim 7, wherein each of the plurality of second concentric conductive loops has a gap to facilitate series connection of the plurality of second concentric conductive loops.

9. The coil of claim 8, wherein the gap associated with one of the plurality of first concentric conductive loops is offset from the gap associated with one of the plurality of second concentric conductive loops.

10. The coil of claim 1, wherein a first innermost conductive loop of the plurality of first concentric conductive loops is coupled to an RF energy source and a second innermost conductive loop of the plurality of second concentric conductive loops is coupled to a reference node.

11. The coil of claim 1, wherein the coil is coupled to a measurement circuit capable of determining a change in impedance of the coil.

12. A method for providing a coil for magnetic induction tomography imaging, the method comprising:
    arranging a plurality of first concentric conductive loops in a first plane on a multilayer printed circuit board;
    arranging a plurality of second concentric conductive loops in a second plane on the multilayer printed circuit board;
    coupling the plurality of first concentric conductive loops in series using a plurality of first connection traces; and
    coupling the plurality of second concentric conductive loops in series using a plurality of second connection traces;
    wherein the plurality of first connection traces and the plurality of second connection traces are radially aligned to connect the plurality of first concentric conductive loops and the plurality of second concentric conductive loops in series such that a current flow of one of the plurality of first connection traces is opposite a current flow of one of the plurality of second connection traces.

13. The method of claim 12, wherein the first plane and the second plane are separated by a plane separation distance.

14. The method of claim 13, wherein the plane separation distance is selected such that the plurality of first concentric conductive loops and the plurality of second concentric conductive loops approximate a single plane of concentric conductive loops in a model used for magnetic induction tomography imaging.

15. The method of claim 14, wherein the plane separation distance is selected to be in the range of about 0.2 mm to about 0.7 mm.

16. The method of claim 12, wherein the method comprises coupling a first innermost conductive loop of the plurality of first concentric conductive loops to an RF energy source and coupling a second innermost conductive loop of the plurality of second concentric conductive loops to a reference node.

17. A system for magnetic induction tomography imaging, comprising:
    an RF energy source;
    a coil coupled to the RF energy source, the coil comprising a plurality of first concentric conductive loops located within a first plane, the plurality of first concentric conductive loops connected in series with one another; the coil further comprising a plurality of second concentric conductive loops located within a second plane, the plurality of second concentric conductive loops connected in series with one another; and
    a measurement circuit capable of obtaining a measurement of an electrical parameter of the coil when the coil is placed adjacent to a specimen;
    wherein the first plane and the second plane are separated by a plane separation distance, the plane separation distance selected such that the plurality of first concentric conductive loops and the plurality of second concentric conductive loops approximate a single plane of concentric conductive loops in a model used for magnetic induction tomography imaging.

18. The system of claim 17, wherein the measurement circuit comprises:
    a phase measurement circuit configured to measure a phase angle between a current and a voltage associated with the coil; and
    a voltage gain measurement circuit configured to measure a voltage gain based at least in part on the voltage associated with the coil and a voltage across a sense resistor coupled in series with the coil.

19. The system of claim 17, wherein the RF energy source is coupled to an innermost conductive loop of the plurality of first concentric conductive loops.

20. The system of claim 18, wherein the coil comprises a plurality of radially aligned connection traces connecting the plurality of first concentric conductive loops and the plurality of second concentric conductive loops in series such that a current flow of one of the plurality of connection traces located in the first plane is opposite a current flow of one of the plurality of connection traces located in the second plane.

21. The coil of claim 1, wherein the specimen comprises a tissue specimen.

22. The coil of claim 21, wherein the tissue specimen comprises a human tissue specimen.

* * * * *